(12) United States Patent
Hassler, Jr. et al.

(10) Patent No.: US 7,727,141 B2
(45) Date of Patent: Jun. 1, 2010

(54) MAGNETIC RESONANCE IMAGING (MRI) SAFE REMOTELY ADJUSTABLE ARTIFICAL SPHINCTER

(75) Inventors: William L. Hassler, Jr., Cincinnati, OH (US); Daniel F. Dlugos, Jr., Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1263 days.

(21) Appl. No.: 11/121,912

(22) Filed: May 4, 2005

(65) Prior Publication Data

US 2006/0252982 A1 Nov. 9, 2006

(51) Int. Cl.
*A61F 13/00* (2006.01)

(52) U.S. Cl. .................................. 600/37; 606/158
(58) Field of Classification Search ............. 600/29–32, 600/37; 606/151, 153, 157
See application file for complete search history.

(56) References Cited

U.S. PATENT DOCUMENTS

| | | | |
|---|---|---|---|
| 4,143,661 A | 3/1979 | LaForge et al. | |
| 4,592,339 A | 6/1986 | Kuzmak et al. | |
| 5,226,429 A | 7/1993 | Kuzmak | |
| 5,449,368 A | 9/1995 | Kuzmak | |
| 6,067,991 A * | 5/2000 | Forsell | 128/899 |
| 6,102,922 A | 8/2000 | Jakobsson et al. | |
| 6,461,292 B1 | 10/2002 | Forsell | |
| 6,461,293 B1 | 10/2002 | Forsell | |
| 6,470,892 B1 | 10/2002 | Forsell | |
| 6,547,716 B1 * | 4/2003 | Milbocker | 600/37 |
| 7,351,240 B2 | 4/2008 | Hassler, Jr. et al. | |
| 7,374,565 B2 | 5/2008 | Hasser, Jr. et al. | |
| 7,390,294 B2 | 6/2008 | Hassler, Jr. | |
| 7,481,763 B2 | 1/2009 | Hassler, Jr. et al. | |
| 7,601,162 B2 | 10/2009 | Hassler, Jr. et al. | |
| 2003/0105385 A1 | 6/2003 | Forsell | |
| 2003/0114729 A1 | 6/2003 | Forsell | |
| 2005/0143765 A1 | 6/2005 | Bachmann et al. | |
| 2005/0143766 A1 * | 6/2005 | Bachmann et al. | 606/158 |
| 2005/0267406 A1 | 12/2005 | Hassler, Jr. | |

FOREIGN PATENT DOCUMENTS

WO   WO 2004/014245   2/2004

OTHER PUBLICATIONS

European Search Report dated Mar. 26, 2008 for Application No. EP06252355.

* cited by examiner

*Primary Examiner*—Charles A Marmor, II
*Assistant Examiner*—Carrie Harris
(74) *Attorney, Agent, or Firm*—Frost Brown Todd LLC

(57) ABSTRACT

An implantable artificial sphincter system provides long-term adjustment via transcutaneous energy transfer (TET), minimizing invasive adjustment through adding or removing fluid via a syringe. An infuser device provides bi-directional fluid transfer via a flexible conduit to a sphincter band, such as a gastric band. Materials are nonferrous and nonmagnetic so as to be magnetic resonance imaging (MRI) safe, being substantially immune to strong magnetic fields and not introducing an electromagnetic interference/compatibility (EMIC) hazard.

14 Claims, 4 Drawing Sheets

MAGNETIC RESONANCE IMAGING (MRI) SAFE REMOTELY ADJUSTABLE ARTIFICAL SPHINCTER

CROSS REFERENCE TO RELATED APPLICATIONS

The present application is related to and claims the benefit of five commonly-owned applications:

"PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857,762, filed 28 May 2004, now U.S. Pat. No. 7,390,294;

"METAL BELLOWS POSITION FEEDBACK FOR HYDRAULIC CONTROL OF AN ADJUSTABLE GASTRIC BAND" to William L. Hassler, Jr., Daniel F. Dlugos, Jr., Rocco Crivelli, Ser. No. 10/856,971, filed 28 May 2004, now U.S. Pat. No. 7,481,763;

"THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857,315, filed 28 May 2004, now U.S. Pat. No. 7,351,240;

"BI-DIRECTIONAL INFUSER PUMP WITH VOLUME BRAKING FOR HYDRAULICALLY CONTROLLING AN ADJUSTABLE GASTRIC BAND" to William L. Hassler, Jr., Daniel F. Dlugos, Jr., Ser. No. 10/857,763, filed 28 May 2004, now U.S. Pat. No. 7,374,565; and "ACTUATOR FOR AN IMPLANTABLE BAND" to William L. Hassler, Jr., Daniel F. Dlugos, Jr., Ser. No. 11/036,460, filed 14 Jan. 2005, now U.S. Pat. No. 7,601,162, the disclosure of all five being hereby incorporated by reference in their entirety.

FIELD OF THE INVENTION

The present invention relates, in general, to medically implantable, remotely-controlled devices that are safe in a magnetic resonance imaging (MRI) environment, and more particularly to such devices that incorporate internal fluid control to adjust an artificial sphincter.

BACKGROUND OF THE INVENTION

Since the early 1980s, adjustable gastric bands have provided an effective alternative to gastric bypass and other irreversible surgical weight loss treatments for the morbidly obese. The gastric band is wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

An artificial sphincter may be utilized in any number of applications within a patient's body where it is desirable to vary the size of an orifice or organ. Depending upon the application, artificial sphincters may take the form of a flexible, substantially non-extensible band containing an expandable section that is capable of retaining fluids. The expandable section would be capable of expanding or contracting, depending upon the volume of fluid contained therein. One particular example of an artificial sphincter is an adjustable gastric banding device, such as described in U.S. Pat. Nos. 4,592,339, 5,226,429, 6,102,922, and 5,449, 368, the disclosure of each being hereby incorporated by reference. Adjustable gastric band implants have a hollow elastomeric balloon with fixed end points encircling a patient's stomach just inferior to the esophago-gastric junction. When saline solution is delivered into the hollow balloon, the gastric band swells and constricts the stomach, for example, for obesity reduction. Different degrees of constriction are desired, and adjustment is required over time as the patient's body adapts to the constriction.

Adding or removing saline solution from the adjustable gastric band is typically accomplished by injection through a fluid injection port to achieve a desired diameter. Since adjustable gastric bands may remain in the patient for long periods of time, the fluid injection port is typically installed subcutaneously to reduce the likelihood of infection. Adjusting the amount of fluid in the adjustable gastric band is achieved by inserting a Huber tip needle through the skin into a silicon septum of the injection port. Once the needle is removed, the septum seals against the hole by virtue of compressive load generated by the septum. A flexible conduit communicates between the injection port and the adjustable gastric band.

While subcutaneously implanted injection ports are a successful approach to readily adjusting a gastric band, and are a desirable feature to retain for initial installation or as a backup, it would be desirable to remotely adjust the gastric band. Although minimally invasive, insertion of the Huber needle to adjust the saline solution volume does introduce increased risk of infection. In addition, this procedure typically entails the inconvenience and expense of scheduling time with a surgeon.

Incorporating remote control of an implanted artificial sphincter would be desirable; however, adjustable gastric bands such as those described above are currently fabricated out of material that does not pose significant limitations on the patient. In particular, increasingly Magnetic Resonance Imaging (MRI) is used as a diagnostic tool and as an aid in performing minimally invasive surgical procedures. MRI operates by creating a strong DC magnetic field (e.g., 0.5-1.5 Teslas) and then disturbing the DC magnetic field with magnetic impulses that induce a weak radio frequency (RF) signal to be emitted by the tissue of a patient. Thus, it is desirable that implantable medical devices contain no ferrous material that would be attracted by the strong DC magnetic field. Otherwise, tissue damage, patient discomfort, or malfunction of the implantable medical device may occur. Further, it is desirable that the medical device not interfere with the weak radio frequency that is produced by the patient, or else artifacts may be created in the diagnostic image that degrade its value.

Efforts have been made to produce other types of implantable devices with actuators that can endure the environment of an MRI machine to some degree. For example, it is known to implant a drug dispensing infuser pump that operates with an electrical DC motor. The deleterious effects of magnetizing the ferrous materials of the DC motor therein is countered by a degree by over-building the device such that operation may continue in a degraded condition. Further, the size of the structural attachments to the DC motor have to be greatly increased to withstand the magnetic attraction that the MRI machine imposes, as well as avoid tissue damage and discomfort by increasing the overall size of the implant, which is not otherwise a desirable design constraint.

It is also known to incorporate MRI safe devices such as a piezoelectric motor into an peristaltic pump, also for drug dispensing. However, peristaltic pumps are unsuitable for long-term intermittent bi-directional fluid control. Even modest leakage past the peristaltic pump during inactive periods would prove unsuitable for fluid control of implants.

Consequently, a significant need exists for a remotely controllable implantable artificial sphincter apparatus that would be MRI safe.

BRIEF SUMMARY OF THE INVENTION

The invention overcomes the above-noted and other deficiencies of the prior art by providing an artificial sphincter assembly that includes an external programmer portion that is at least intermittently in communication with an implantable artificial sphincter portion for remote adjustment thereof. The implantable artificial sphincter portion has an artificial sphincter band formed of biocompatible and nonferromagnetic material sized to encompass a body lumen. Once implanted and adjusted to an initial internal circumference, control circuitry is responsive to adjustment commands from the external programmer portion that in turn are used to activate an MRI safe actuator to selectively bi-directionally adjust the artificial sphincter. A power source powers both the control circuitry and the actuator. Thereby, a remotely controllable artificial sphincter is provided that does not require piercing the skin with a needle. Further, the implantable portion of the device is MRI safe, allowing the recipient to take advantage of this important diagnostic tool.

In one aspect of the invention, the artificial sphincter apparatus incorporates an MRI safe piezoelectric motor that is activated by the control circuitry to selectively bi-directionally adjust the artificial sphincter.

In another aspect of the invention, an artificial sphincter made of biocompatible and nonferromagnetic material is sized to encompass a body lumen that is responsive to a transmission to convert an actuator motion from an MRI safe actuator to an adjustment of the inner circumference of the artificial sphincter band.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
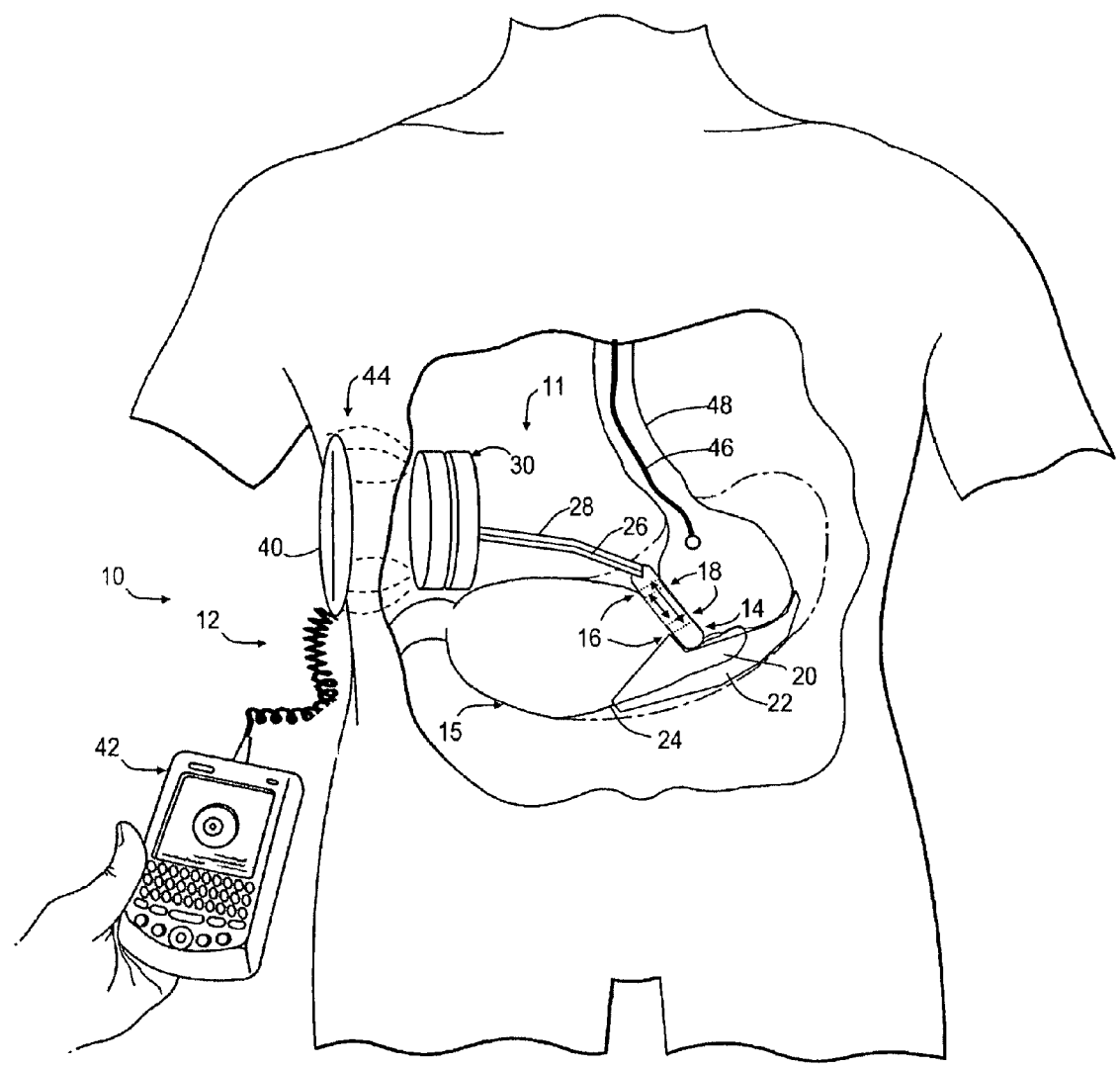
FIG. 1 is a front diagrammatic view of an implantable artificial sphincter apparatus encircling an upper portion of a patient's stomach to form a remotely adjustable stoma for treatment of morbid obesity.

In FIG. 1, an artificial sphincter system is used to constrain a bodily lumen. More particularly, in the illustrative version, an adjustable gastric band (AGB) apparatus 10 is used to treat morbid obesity. Advantageously, the various components of an implanted portion 11 of the AGB apparatus 10 comprise materials that are at least Magnetic Resonance Imaging (MRI) safe, being nonferrous and nonferromagnetic. Yet, the implanted portion 11 may be intermittently remotely adjusted transcutaneously in response to an external portion 12 that need not be MRI safe. Between adjustments, the implanted portion 1 remains at a current setting for long durations.

To that end, a gastric band 14 encircles and constrains a stomach 15, forming a stoma that is remotely adjustable between a larger diameter depicted at 16 and a narrower diameter depicted at 18. The gastric band 14 may be held in place by drawing a flap 20 of a lower portion 22 of the stomach 15 over the gastric band 14 and suturing the flap 20 to an upper portion 24 of the stomach 15. The gastric band 14 thus encourages weight loss by limiting the patient to small meals because the stoma 18 slows movement of food from the upper portion 24 to the lower portion 22 of the stomach 15. Additionally, food remaining in the upper portion 24 of the stomach 15 stimulates nerves that indicate fullness.

The inner diameter of the gastric band 14 is responsive to movement of a motion transfer medium 26 guided within a conduit 28. The motion transfer medium 26 may be a fluid (e.g., saline) or a translating or rotating cable. This movement is in response to an implanted actuator 30 that generates this movement of the transfer medium 26. It should be appreciated for clinical flexibility and clarity in the description herein that the implanted actuator 30 is spaced apart from the gastric band 14. However, the implanted actuator 30 may be integrally attached to the gastric band 14, reducing significantly any length of required transmission elements such as conduit 28 and motion transfer medium 26.

The implantable portion 11 of the AGB apparatus 10 is remotely controllable by an emitter 40 which is controlled by a programmer 42, both part of the external portion 12 of the AGB apparatus 10. In particular, the emitter 40 sends transcutaneous signals (e.g., AC magnetic field, RF broadcast, coded message on an ultrasonic carrier, etc.) 44 that are received by the implantable portion 11. Feedback as to the desired inner circumference of the gastric band 14 and/or size of the stoma 14, 16 may be deduced by an amount of movement corresponding to the motive transfer medium 26 movement that is internally sensed by the implantable portion 11. Alternatively or in addition, a noninvasive imaging device, such as an endoscope 46, is inserted down the esophagus 48 and/or an ultrasonic transceiver 49 (FIG. 2).

An advantageous approach to further reducing the necessary size of the implantable actuator 30 is to utilize transcutaneous energy transfer (TET) for powering motive adjustment operations. Telemetry may also be utilized for functions such as commanding and/or monitoring the current position and/or amount of adjustment travel available, especially if completing closed-loop adjustment control of the gastric band 14 external to the patient.

Figure 2:
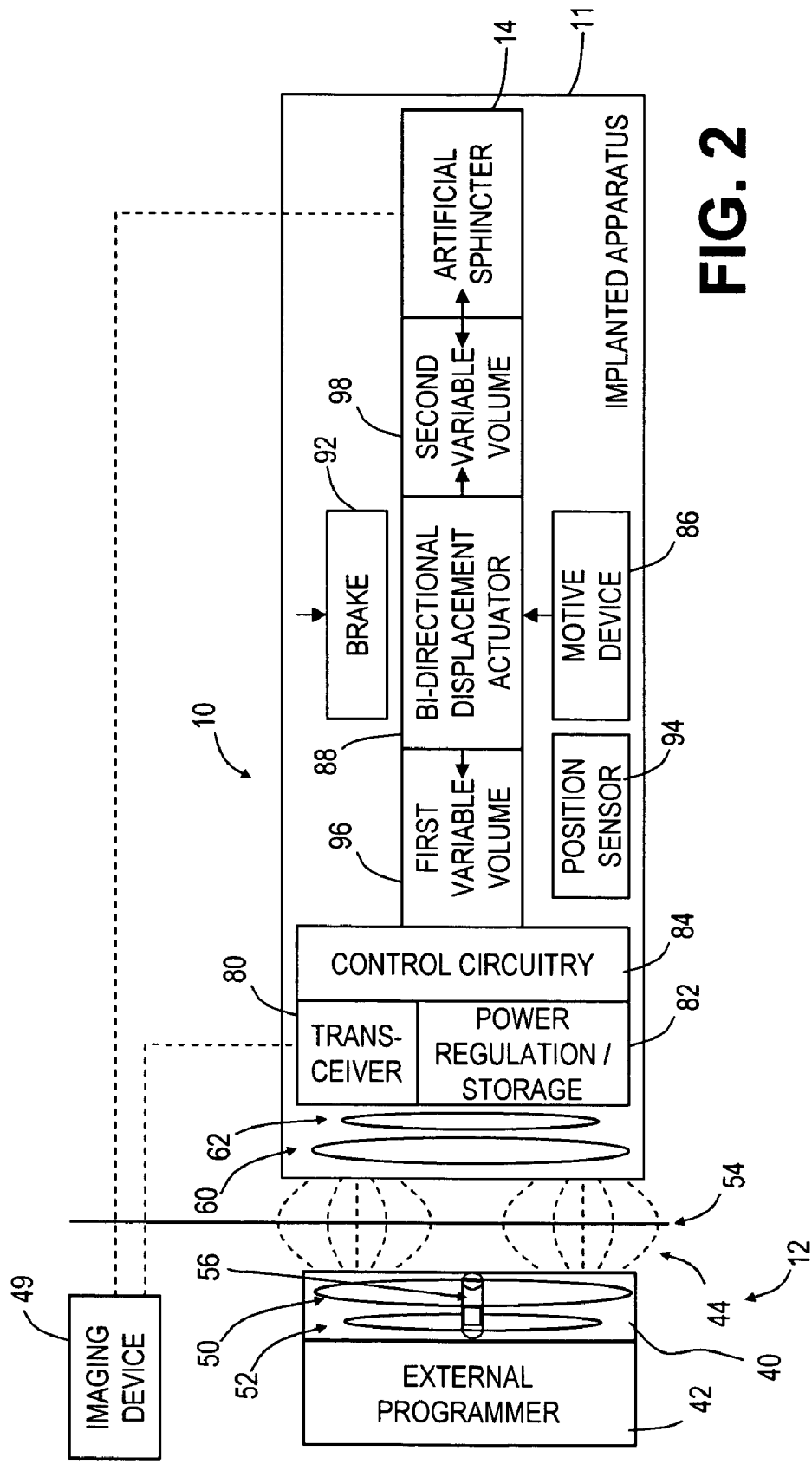
FIG. 2 is a functional block diagram of the implantable artificial sphincter apparatus of FIG. 1.

In FIG. 2, the emitter 40 is depicted as comprising a TET transceiver further comprising an external TET coil 50 and a co-axial external telemetry coil 52; the two coils 50, 52 are electrically separate and have a different resonant frequency for simultaneous TET and telemetry through the skin 54 of the patient. A ferrite core 56 may be placed along the axis of the coils 50, 52 to further enhance the efficient depth of TET to correspond to an implanted TET coil 60 and a co-axial implanted telemetry coil 62 which are incorporated into the implanted portion 11 of the AGB apparatus 10.

Efficient power coupling of external and implanted TET coils is described in four co-pending and commonly-owned patent applications filed on 24 Jun. 2004, all of which are hereby incorporated by reference in their entirety, (1) "TRANSCUTANEOUS ENERGY TRANSFER PRIMARY COIL WITH A HIGH ASPECT FERRITE CORE", Ser. No. 10/876,313; (2) "MEDICAL IMPLANT HAVING CLOSED LOOP TRANSCUTANEOUS ENERGY TRANSFER (TET) POWER TRANSFER REGULATION CIRCUITRY", Ser. No. 10/876,038; (3) "SPATIALLY DECOUPLED TWIN SECONDARY COILS FOR OPTIMIZING TRANSCUTANEOUS ENERGY TRANSFER (TET) POWER TRANSFER CHARACTERISTICS", Ser. No. 10/876,057; and (4) "LOW FREQUENCY TRANCUTANEOUS ENERGY TRANSFER TO IMPLANTED MEDICAL DEVICE", Ser. No. 10/876,307.

The implanted portion 11 includes transceiver circuitry 80 that sends data parameters and receives control commands by inductive coupling of the external telemetry coil 62 with the external telemetry coil 52. The implanted TET coil 60 is in electrical communication with power regulation/storage circuitry 82 for recharging on-board power storage and/or buffering. Control circuitry 84, powered by the power regulation/storage circuitry 82 and responsive to commands received by transceiver 80, bi-directionally activates a motive device 86 that effects movement of a bi-directional displacement actuator 88. Examples of a motive device that effects a bi-directional displacement actuator are described in the above-referenced patent application Ser. Nos. 10/857,762 and 10/857,315 wherein MRI safe electromechanical devices such as piezoelectric motors and thermodynamically adjusted bellows accumulators are described.

For motive devices 86 that do not impose an inherent locking effect to the bi-directional displacement actuator 88 when deactivated, the control circuitry 84 may advantageously also activate a brake 92 to release the bi-directional displacement actuator 88 during adjustment. An example of a brake is described in the above-referenced application Ser. No. 10/857,763, wherein a piezoelectrically released brake caliber allows a bellows accumulator to change volumes.

This adjustment may advantageously be monitored by an internal position sensor 94 so as to determine a differential change in a first variable volume 96 and a second variable volume 98. An example of monitoring volumes is described in the above-referenced patent application Ser. No. 10/856,971 wherein the first volume is contained within a bellows accumulator that is coupled to a position sensor within an encompassing case. It should be appreciated that sensing may be incorporated into a motive element, a transmission element, or a parameter of the artificial sphincter representative of its adjusted size. It should be appreciated that the volume adjustment may be contained within an implanted device spaced apart from the artificial sphincter band as described in the above-referenced patent application Ser. No. 11/036,460 wherein a first volume in a bellows accumulator controls a second volume in a bellows piston accumulator that elongates within a conduit to selectively push and pull an elongate flexible rod whose motion affects the adjustment of the band.

Figure 3:
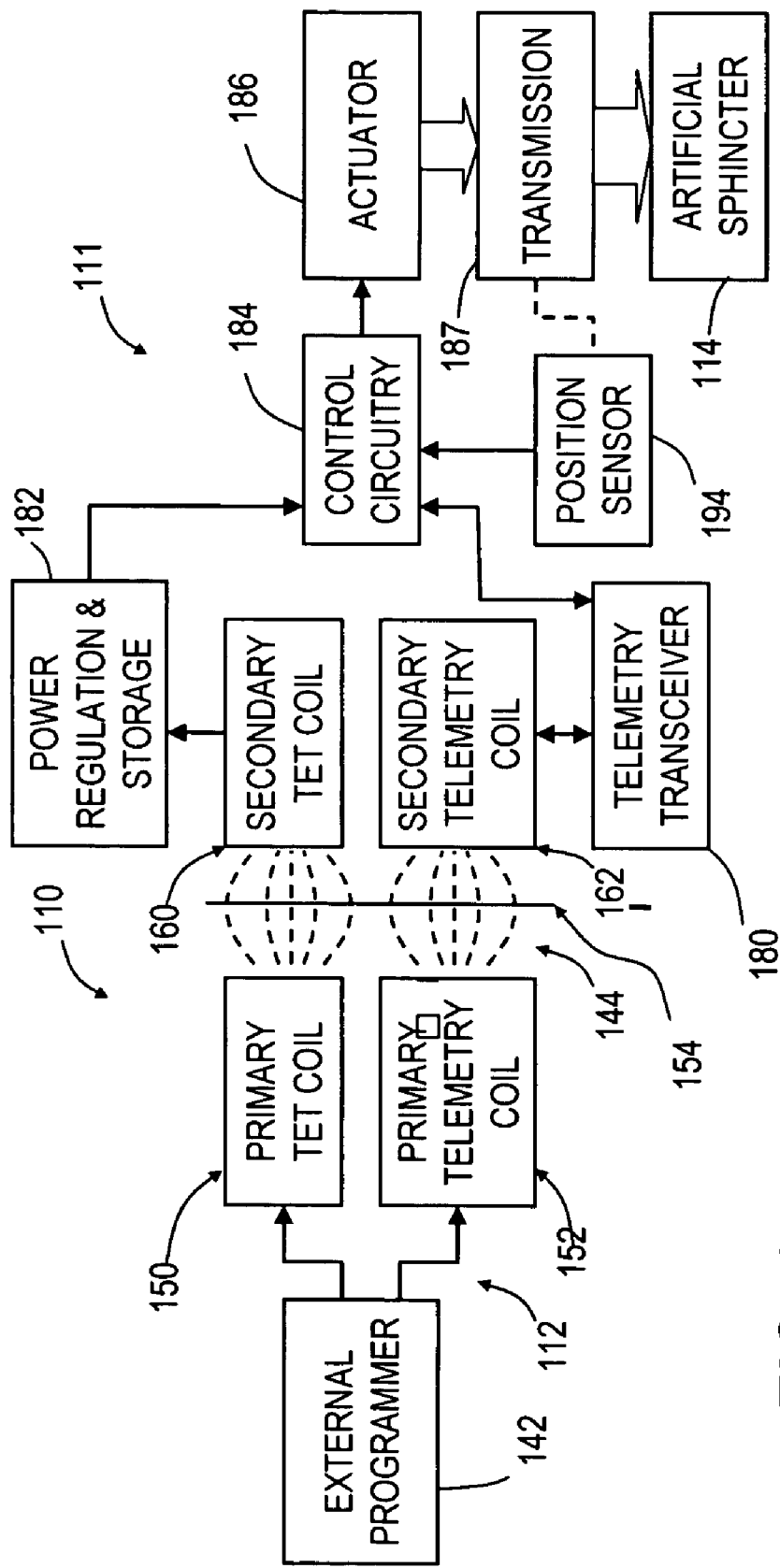
FIG. 3 is a control diagram of an alternative artificial sphincter apparatus of FIG. 2.

In FIG. 3, an alternative adjustable gastric band (AGB) apparatus 110 that is remotely controllable is used to treat morbid obesity. Advantageously, the various components of an implanted portion 111 of the AGB apparatus 110 comprise materials that are at least Magnetic Resonance Imaging (MRI) safe, being nonferrous and nonferromagnetic. Yet, the implanted portion 111 may be intermittently remotely adjusted transcutaneously in response to an external portion 112 that need not be MRI safe. Between adjustments, the implanted portion 111 remains at a current setting for long durations.

To that end, an artificial sphincter 14 encircles and constrains a body lumen (not shown in FIG. 3). The implantable portion 111 of the AGB apparatus 110 is remotely controllable by an external programmer 142, which sends TET signals 144 that are received by the implantable portion 111. In particular, an external TET coil 150 and an external telemetry coil 152 are electrically separate and have a different resonant frequency for simultaneous TET and telemetry through skin 154 of the patient to an implanted TET coil 160 and an implanted telemetry coil 162 respectively incorporated into the implanted portion 111 of the AGB apparatus 110.

The implanted portion 111 includes transceiver circuitry 180 that sends data parameters and receives control commands by inductive coupling of the implanted telemetry coil 162 with the external telemetry coil 152. The implanted TET coil 160 is in electrical communication with power regulation/storage circuitry 182 for recharging on-board power storage and/or power buffering. Control circuitry 184 is powered by the power regulation/storage circuitry 182 and is responsive to commands received by transceiver 180 and to a position sensor 194 to bi-directionally activate an actuator 186 that acts through a transmission 187 to adjust the artificial sphincter 114. Confirmation of adjustment may be sent via a message initiated by control circuitry 182 through telemetry transceiver 180 through the implanted telemetry coil 162 to the external telemetry coil 152 to the external programmer 142. The depicted actuator 186 and transmission 187 have an inherent locking effect such that when deactivated, the artificial sphincter 114 retains the adjusted size.

Figure 4:
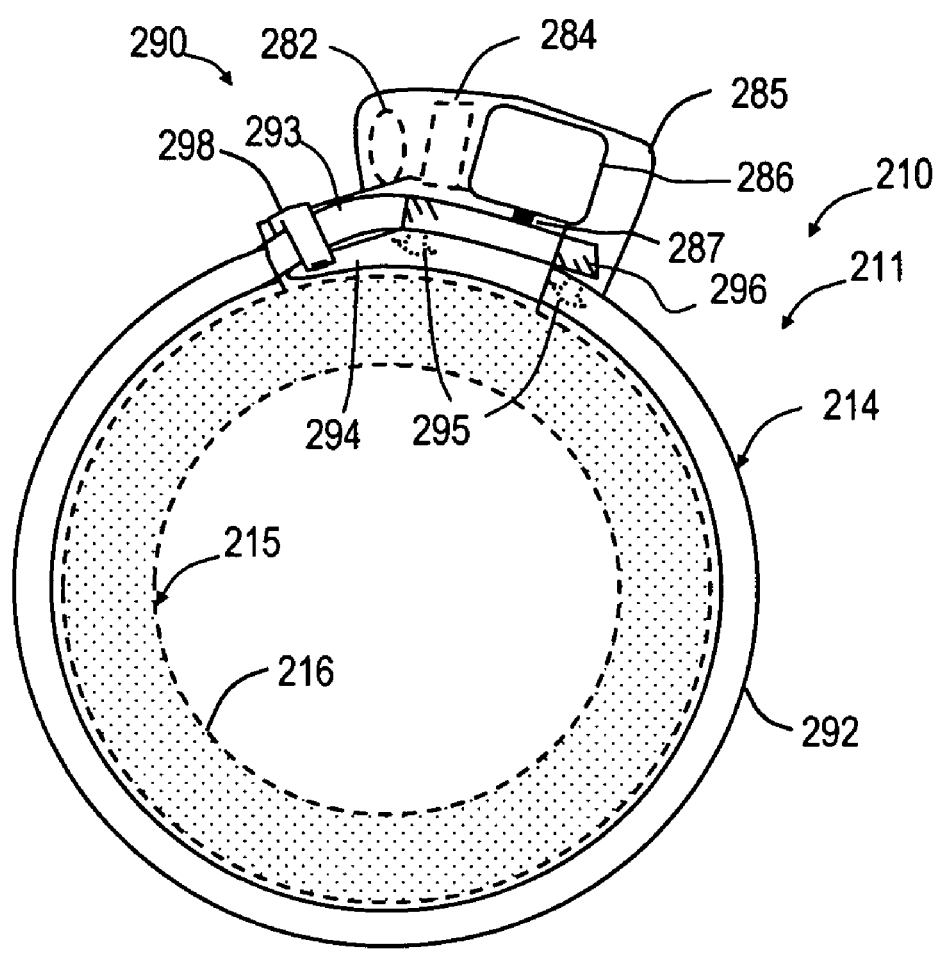
FIG. 4 is a diagrammatic view of an alternative remotely controlled artificial sphincter apparatus having integral piezoelectric actuation.

In FIG. 4, an illustrative version of an AGB apparatus 210 that integrates many features in an implantable portion 211, and more particularly an MRI safe electromechanical adjustment system 290, is incorporated into an adjustable artificial sphincter 214 that encompasses a body lumen 215 to form a narrowed or closed stoma 216. A controller housing 285 advantageously incorporates a stored power source 282 that powers both control circuitry 284, that is responsive to external adjustment commands, and a piezoelectric motor 286, whose selectively oscillating drive tip 287 directly adjusts the circumference of a band 292, inherently acting as both transmission during adjustment and a brake when deactivated.

The band 292 is formed of biocompatible and MRI safe material (e.g., silicone) that may be sized for the intended initial circumference by trimming a first end 294 or selecting a band 292 of appropriate length. The controller housing 285 is attached to an external surface of the first end. For versions wherein the first end 294 is trimmed, the controller housing 285 may include attachment features 295 that engage the band 292 at an appropriate location. The other end 293 of the band 292 is passed through a buckle 298 attached to the first end 294. The other end 293 terminates in a ceramic actuated tab 296 and is pinched between the first end 294 and the driving tip 287 of the piezoelectric motor 286 that responds to oscillations in one direction from the driving tip 287 by drawing more of the band 292 through the buckle 298 and to the other direction by pushing more of the band 292 back through the buckle 298.

It should be appreciated with the benefit of the present disclosure that in FIG. 4 the active components may be spaced away from the band 292, mechanically coupled thereto by a control cable (not shown) that communicates by either rotation or translation.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, it will become readily apparent to those skilled in the art that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. patent application 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. patent application Publ. No. 2003/0114729, which is hereby incorporated herein by reference.

What is claimed is:

1. An apparatus, comprising an external programmer portion at least intermittently in communication with an implantable artificial sphincter portion for remote adjustment thereof, the implantable artificial sphincter portion comprising:
   an artificial sphincter band formed of biocompatible and nonferromagnetic material sized to encompass a body lumen, wherein the artificial sphincter band comprises a ceramic actuating end and a first end, wherein the ceramic actuating end is in opposing and sliding contact with the first end;
   control circuitry responsive to the external programmer portion;
   an MRI safe piezoelectric motor attached to the first end of the artificial sphincter band, wherein the MRI safe piezoelectric motor includes a drive tip in actuating contact with the ceramic actuating end, wherein the MRI safe piezoelectric motor is activated by the control circuitry to selectively, bi-directionally adjust the artificial sphincter;
   a power source providing power to the control circuitry and to the MRI safe piezoelectric motor; and
   a transmission communicating an output motion from the MRI safe piezoelectric motor to the artificial sphincter band, wherein the transmission comprises conduit containing fluid, the conduit extending from the MRI safe piezoelectric motor to the artificial sphincter band, the artificial sphincter band further comprising a bladder responsive to bi-directional fluid flow from the conduit induced by the MRI safe piezoelectric motor to adjust an internal circumference of the artificial sphincter band.

2. The apparatus of claim 1, wherein the power source comprises a battery.

3. The apparatus of claim 1, wherein the power source comprises transcutaneous energy transfer (TET), the implantable artificial sphincter portion further comprising an implantable TET coil electromagnetically tuned to receive TET from the external programmer portion and to provide the received TET to the power source.

4. The apparatus of claim 1, further comprising a position sensor operatively configured to sense a position related to an internal circumference of the artificial sphincter band.

5. An apparatus, comprising an external programmer portion at least intermittently in communication with an implantable artificial sphincter portion for remote adjustment thereof, the implantable artificial sphincter portion comprising:
   an artificial sphincter band formed of biocompatible and nonferromagnetic material sized to encompass a body lumen; control circuitry responsive to the external programmer portion;
   an MRI safe piezoelectric motor activated by the control circuitry to selectively bi-directionally adjust the artificial sphincter band; and
   a power source providing power to the control circuitry and to the actuator;
   wherein the artificial sphincter band includes a rigid actuating end, the piezoelectric motor being attached to a first end of the artificial sphincter band, the piezoelectric motor including a drive tip in actuating contact with the rigid actuating end, which in turn is in opposing, sliding contact with the first end.

6. The apparatus of claim 5, wherein the power source comprises a battery.

7. The apparatus of claim 5, wherein the power source comprises transcutaneous energy transfer (TET), the implantable artificial sphincter portion further comprising a implantable TET coil electromagnetically tuned to receive TET from the external programmer portion and to provide the received TET to the power source.

8. An apparatus, comprising an external programmer portion at least intermittently in communication with an implantable artificial sphincter portion for remote adjustment thereof, the implantable artificial sphincter portion comprising:
   an artificial sphincter band formed of biocompatible and nonferromagnetic material sized to encompass a body lumen and including an adjustable inner circumference, wherein the artificial sphincter band includes a ceramic actuating end and a first end;
   a transmission operatively configured to convert an actuator motion to an adjustment of the inner circumference of the artificial sphincter band;
   control circuitry responsive to the external programmer portion;
   an MRI safe actuator operatively configured to produce the actuator motion coupled to the transmission and activated by the control circuitry to selectively, bi-directionally adjust the artificial sphincter, wherein the actuator comprises a piezoelectric motor, wherein the piezo electric motor is attached to the first end of the artificial sphincter band and includes a drive tip in actuating contact with the ceramic actuating end of the artificial sphincter band, which in turn is in opposing, sliding contact with the first end; and
   a power source providing power to the control circuitry and to the actuator.

9. The apparatus of claim 8, wherein the power source comprises a battery.

10. The apparatus of claim 8, wherein the power source comprises transcutaneous energy transfer (TET), the implantable artificial sphincter portion further comprising a implantable TET coil electromagnetically tuned to receive TET from the external programmer portion and to provide the received TET to the power source.

11. The apparatus of claim 8, wherein the transmission comprises conduit containing fluid, the artificial sphincter band further comprising a bladder responsive to bi-directional fluid flow from the conduit to adjust an internal circumference of the artificial sphincter band.

12. The apparatus of claim 8, wherein the transmission comprises a transmission cable.

13. The apparatus of claim 12, wherein the transmission cable is operatively configured to communicate a translation motion.

14. The apparatus of claim 8, further comprising a position sensor operatively configured to sense a position related to an internal circumference of the artificial sphincter band, wherein the position sensor is in communication with the control circuitry, wherein the control circuitry is configured to control the MRI safe actuator in accordance with position data communicated from the position sensor.

* * * * *